United States Patent [19]

Mercier

[11] Patent Number: 5,019,098
[45] Date of Patent: May 28, 1991

[54] SIGHT-CORRECTING OPTICAL COMPONENT SUCH AS AN INTRA-OCULAR IMPLANT OR CONTACT LENS

[75] Inventor: Jean-Louis Mercier, Fontenay les Briis, France

[73] Assignee: Essilor International Cie Generale d'Optique, Creteil Cedex, France

[21] Appl. No.: 519,870

[22] Filed: May 7, 1990

[30] Foreign Application Priority Data

May 19, 1989 [FR] France ............................. 89 06594

[51] Int. Cl.$^5$ ............................ A61F 2/16; G02C 7/04
[52] U.S. Cl. .......................................... 623/6; 351/161
[58] Field of Search ......................................... 623/4–6; 351/160 R, 161, 168, 160

[56] References Cited

U.S. PATENT DOCUMENTS

| | | | |
|---|---|---|---|
| 4,469,413 | 9/1984 | Shirayanagi | 350/432 |
| 4,504,982 | 3/1985 | Burk | 623/6 |
| 4,710,193 | 12/1987 | Volk | 623/6 |
| 4,769,033 | 9/1988 | Nordas | 623/6 |

OTHER PUBLICATIONS

Journal of Optical Society of America, vol. 2, No. 8, Aug. 1985, pp. 1273–1281, New York, U.S.; R. Navarro et al.: "Accommodation–Dependent Model of the Human Eye with Aspherics".

Primary Examiner—Ronald Frinks
Attorney, Agent, or Firm—Charles A. Brown

[57] ABSTRACT

An optical component such as an intra-ocular implant or contact lens for correcting sight has an aspherical surface in at least the central part of at least one side. The parameters of this surface are chosen so that for the optical system comprising the optical component and an associated eye model the object proximity curve is a specific shape.

12 Claims, 4 Drawing Sheets

SIGHT-CORRECTING OPTICAL COMPONENT SUCH AS AN INTRA-OCULAR IMPLANT OR CONTACT LENS

BACKGROUND OF THE INVENTION

1. Field of the invention

The present invention is generally concerned with optical components used to correct sight.

It is more particularly directed to intra-ocular implants although it is also applicable to contact lenses.

2. Description of the prior art

As is well known, an intra-ocular implant is designed to replace a defective crystalline lens.

An intra-ocular implant of this kind usually has no ability to accommodate.

This is the case, for example with the implant which is the subject of the U.S. Pat. No. 4,504,982.

In this American patent the central part of the front surface of the intra-ocular implant concerned forms an aspherical surface of revolution with a meridian section satisfying the equation:

$$X = \frac{1}{R}\left[\frac{Y^2}{1 + \sqrt{1 - (1 + K) Y^2/R^2}}\right] + $$
$$A2\ Y^4 + A3\ Y^6 + A4\ Y^8 + A5\ Y^{10}$$

in which R, K, A2, A3, A4 and A5 are numerical parameters. However, considered in its entirety this intra-ocular implant is of constant power, the numerical parameters in question simply being chosen so that most of its longitudinal spherical aberration is corrected.

Similarly, the intra-ocular implant which is the subject of the U.S. Pat. No. 4,769,033 has no ability to accommodate in that, being a bifocal lens, it makes no provision for intermediate vision between far vision and near vision.

The obvious disadvantage of intra-ocular implants of this kind with no ability to accommodate is that they are not inherently satisfactory for all kinds of vision and so require the occasional wearing of eyeglasses, especially in the case of a constant power intra-ocular implant.

An accommodating intra-ocular implant is described in the U.S. Pat. No. 4,710,193, however.

This intra-ocular implant is a diffractive device, however, and in practise causes non-negligible chromatic aberration.

An object of the present invention is an accommodating optical device, in particular in intraocular implant, which is advantageously free of this disadvantage.

Until now intra-ocular implant design calculations have essentially been based on the single power that the implant is required to have, with the implant isolated in air, and without reference to the longitudinal spherical aberration to which the implant gives rise in the eye. The invention departs from this conventional thinking by regarding an intra-ocular implant of this kind, once fitted, as forming one component of an optical system whose other components are part of the eye concerned and by conferring upon the intra-ocular implant the surface shapes required to produce a given longitudinal spherical aberration within this optical system, as estimated by calculation.

The problem arises that the component parts of an eye and therefore their characteristics vary from one person to another.

The invention also proposes to use a particular eye model as a reference standard.

This is preferably the eye model described by R. NAVARRO et al in an article entitled "Accommodation-dependent model of the human eye with aspherics" in J. Opt. Soc. Am. A, vol. 2, No. 8, Aug. 1985 which is incorporated in the application by reference.

A different eye model could equally well be chosen instead of this one, however.

SUMMARY OF THE INVENTION

The present invention consists in a sight-correcting optical component having front and rear surfaces at least one of which has a central part in the form of an aspherical surface of revolution with a meridian section satisfying the equation $$X = \frac{1}{R_1}\left[\frac{Y^2}{1 + \sqrt{1 - (1 + K) Y^2/R_1^2}}\right] + $$
$$A2\ Y^4 + A3\ Y^6 + A4\ Y^8 + A5\ Y^{10}$$

in which R1, K, A2, A3, A4 and A5 are numerical parameters chosen so that for the optical system comprising the optical component and a specified eye model, minus the crystalline lens if the optical component is an intra-ocular implant, they yield for an object proximity P defined by the equation $$P = N' \cdot \frac{dx'}{f'^2}$$

in which N' is the refractive index of the image medium, dx' is the longitudinal spherical aberration in the image space and f' is the focal length of said eye model a representative curve which:

for high values of the distance from the axis comprises a substantially straight first section with a slope less than or equal to zero and entirely located between a vertical line passing through a defined reference origin and an oblique line passing through points with coordinates (−1, 1.5) and (−1.5, 2.75) relative to the reference origin;

for low values of the distance from the axis comprises a second section intersecting the diopter axis vertically between points with horizontal coordinates (−2.5) and (−4) relative to said reference origin, and for intermediate values of the distance from the axis comprises a median section merging monotonically and continuously with the first and second sections.

The optical system comprising the optical component in accordance with the invention and the eye to which it is applied has caustic characteristics at two points representing correct conditions of vision for far vision and for near vision, with a possibility of intermediate vision between the latter, for optimum user comfort.

Especially in the case of an intra-ocular implant substituted for a defective crystalline lens, the invention achieves true restoration of the ability to accommodate lost by the eye, while keeping longitudinal spherical aberration within limits that are naturally acceptable.

In a first embodiment the longitudinal spherical aberration for far vision is that of eye itself.

In a second embodiment it is properly corrected.

In this latter case the proximity is advantageously stabilized for far vision.

The invention and its characteristics and advantages will emerge from the following description given by way of non-limiting example only with reference to the appended diagramatic drawings.

DETAILED DESCRIPTION OF THE INVENTION

Figure 1:
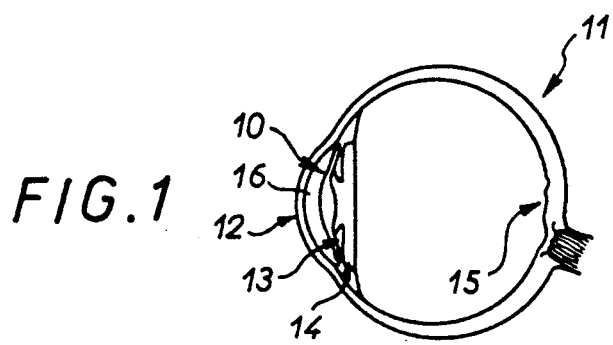
FIG. 1 is a view in axial cross-section of an eye fitted with an optical component in accordance with the invention.
Figure 2:
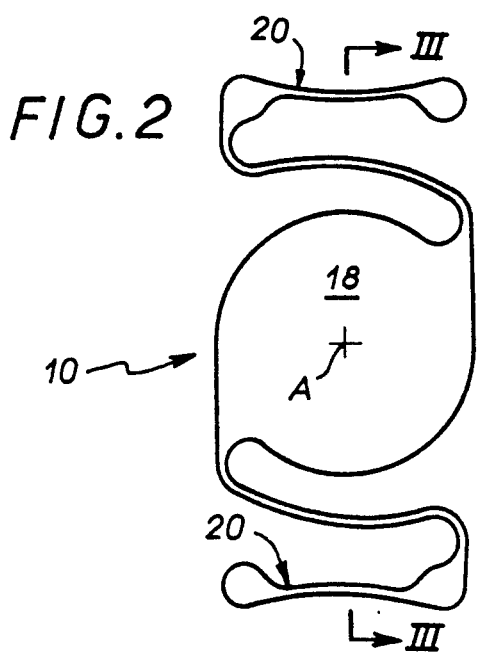
FIG. 2 is a plan view of this optical component to a larger scale.
Figure 3:
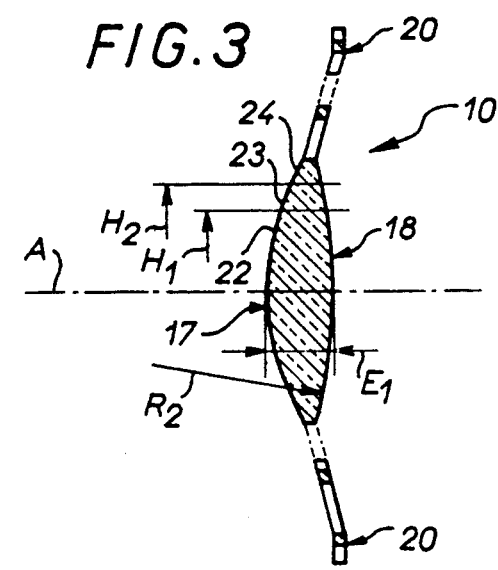
FIG. 3 is a view of it in axial cross-section on the line III—III in FIG. 2.
Figure 6:
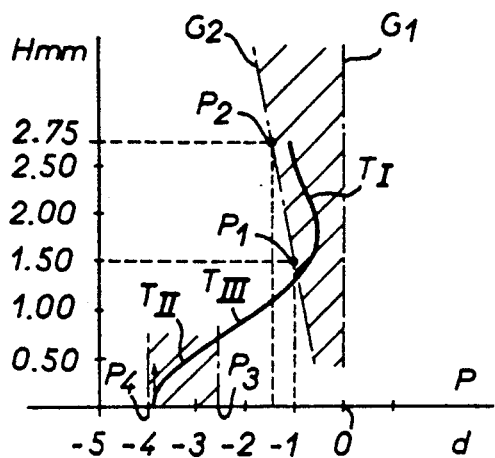
FIG. 6 is a diagram analogous to that of FIG. 6 relating to the object proximity curve of the optical system comprising this eye model and the optical component in accordance with the invention.
Figure 7:
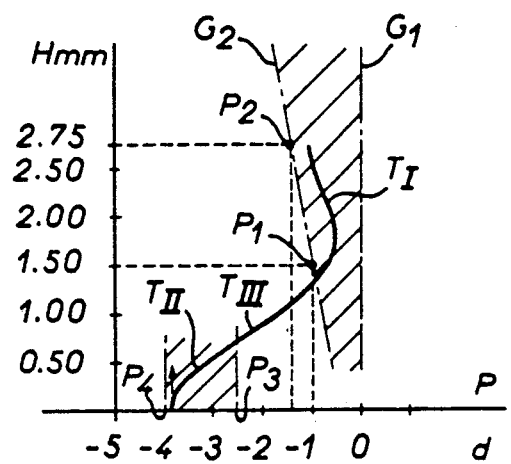
FIGS. 7 through 18 are diagrams analogous to that of FIG. 6 for other optical components in accordance with the invention.
Figure 8:
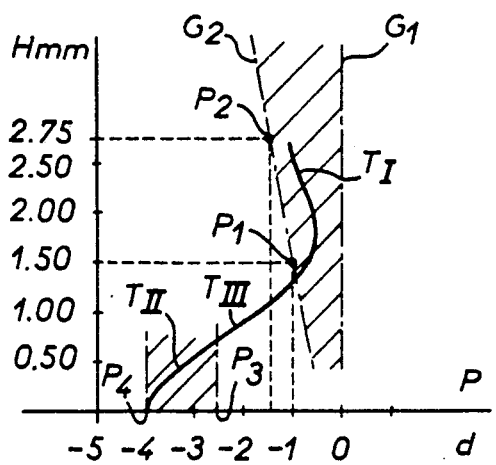
Figure 9:
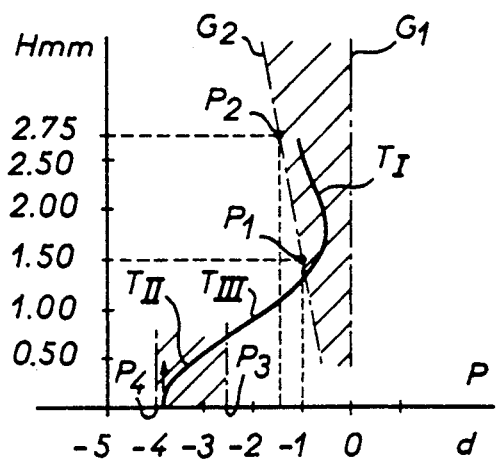
Figure 10:
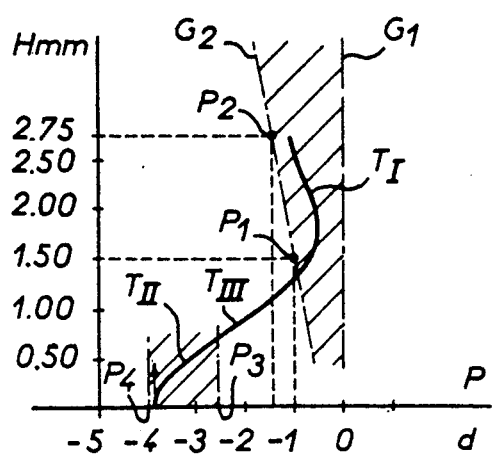
Figure 11:
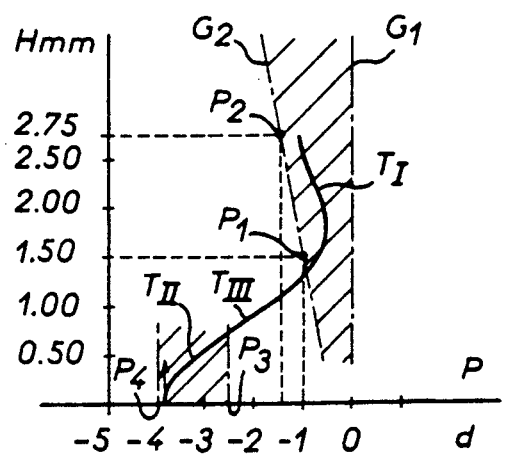
Figure 12:
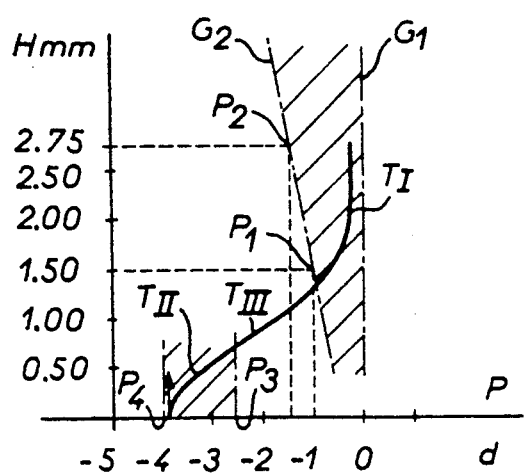
Figure 13:
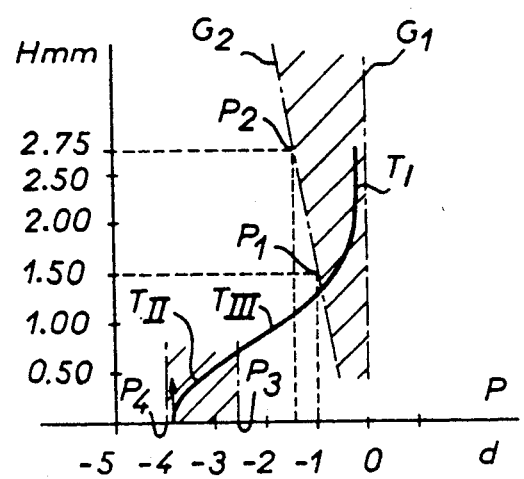
Figure 14:
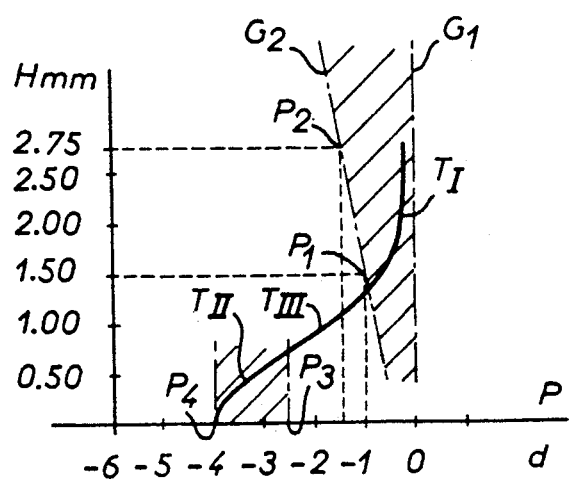
Figure 15:
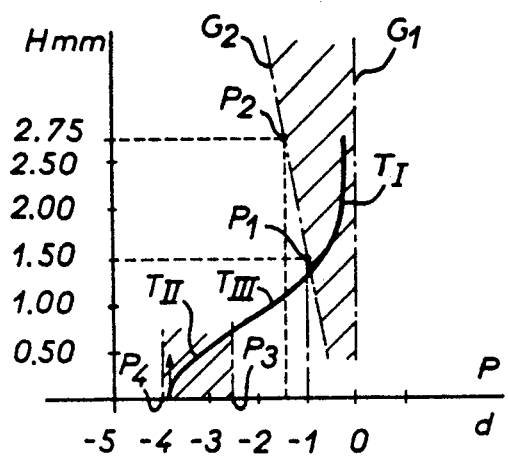
Figure 16:
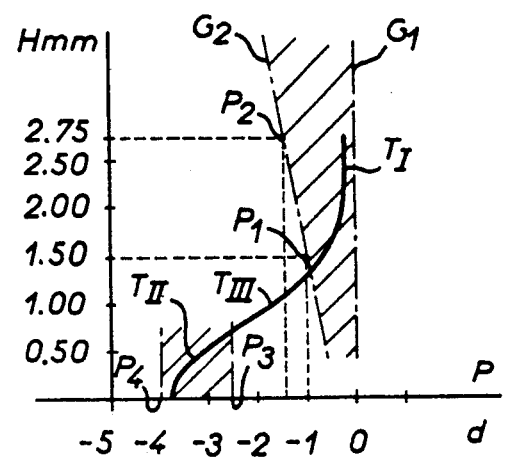
Figure 17:
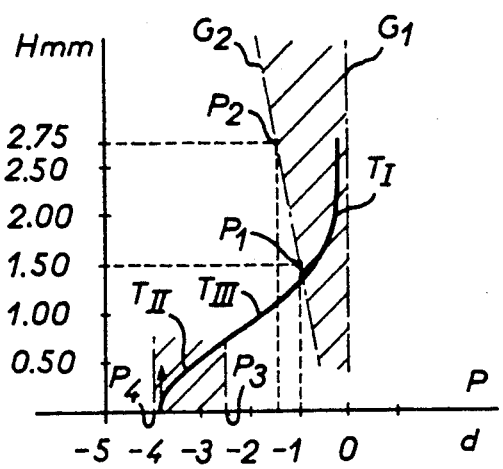
Figure 18:
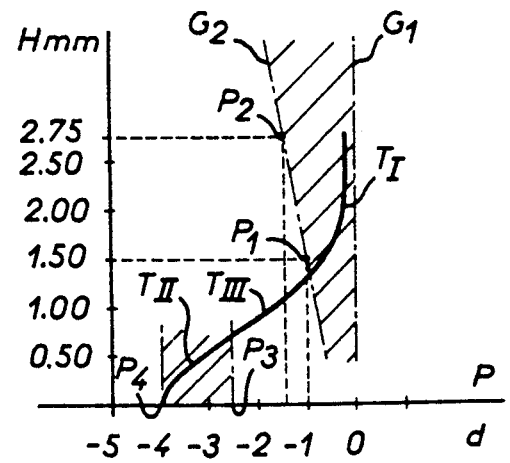

FIGS. 1 through 3 and the associated diagram in FIG. 6 show by way of example the application of the invention to an intra-ocular implant 10 substituted for the crystalline lens of the treated eye 11.

FIG. 1 shows the cornea 12 of the eye 11, its iris 13, the sac 14 that previously contained the crystalline lens and the retina 15.

In the preferred embodiment shown the intra-ocular implant 10 in accordance with the invention is implanted in the anterior chamber 16 of the eye 11, that is to say in the part of the eye between the cornea 12 and the iris 13.

In a way that is known in itself, the intra-ocular implant 10 has a front surface 17 and a rear surface 18 and is provided at its edge with two elastically deformable arms 20 at diametrally opposed positions. Each of these arms is S-shaped and is designed to bear against the ciliary bodies of the eye 11 at the root of the iris 13.

As the corresponding arrangements are well known in themselves and do not of themselves form any part of the present invention they will not be described in more detail here.

They are, incidentally, susceptible to variations, especially with regard to the configuration and/or the number of the arms 20.

Also in a way that is known in itself, the intra-ocular implant 10 may be made from a synthetic material such as a methyl methacrylate polymer.

Let N1 denote the refractive index of the material from which the implant is made and let A denote its axis.

In the embodiment shown in FIGS. 1 through 3 the intra-ocular implant 10 in accordance with the invention is biconvex.

The central part of its front surface 17 is an aspherical surface 22 of revolution with a meridian section satisfying the following equation:

$$X = \frac{1}{R_1}\left[\frac{Y^2}{1 + \sqrt{1 - (1 + K) Y^2/R_1^2}}\right] + A2\ Y^4 + A3\ Y^6 + A4\ Y^8 + A5\ Y^{10}$$

in which R1, K and A2, A3, A4 and A5 are numerical parameters.

In practice R1 corresponds to the radius of curvature of a base sphere, K to a cone angle constant and A2, A3, A4 and A5 to asphericity parameters to be explained later.

In practice the aspherical surface 22 is delimited by a circumference of radius H1 with a maximum value of 2.35 mm.

Beyond this, the peripheral part of the front surface 17 comprises a toroidal surface 23 which merges tangentially with the aspherical surface 22, its radius of curvature being equal to that of the latter where it merges with it.

Let R3 denote this radius of curvature and let X3, Y3 denote the coordinates of the corresponding center.

The toroidal surface 23 advantageously minimizes the consequences of any eccentricity and/or a relatively large (greater than 5.5 mm) diameter pupil.

It also has the advantage of making it possible to control deformations outside the aspherical central surface 22.

In practice the toroidal surface 23 is in turn delimited by a circumference of radius H2 in the order of 3 mm.

Beyond this the intra-ocular implant 10 forms a simple annular bead 24 from which the arms 20 depart.

In the embodiment shown in FIGS. 1 through 3 the rear surface 18 of the intra-ocular implant 10 is spherical.

Let R2 denote its radius.

Finally, let E1 denote its thickness on its axis A.

The design calculations for an intra-ocular implant 10 in accordance with the invention which establish its parameters R1, K, A2, A3, A4 and A5 are related to a particular eye model.

As previously mentioned, this is preferably the eye model of R. NAVARRO et al.

Figure 4:
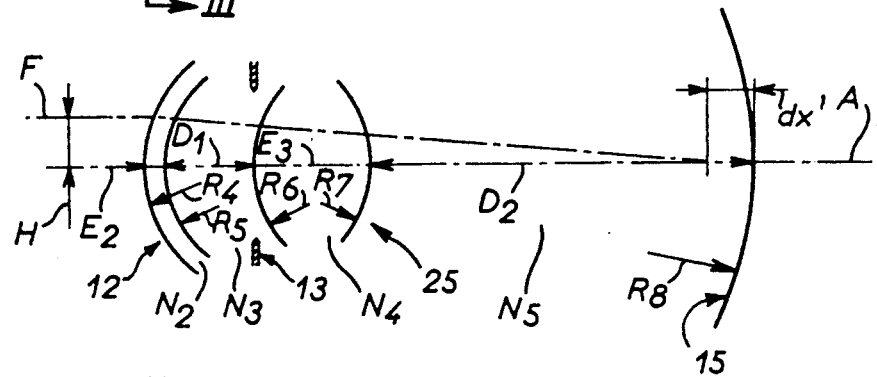
FIG. 4 is a partial view of the eye model used in connection with the invention as seen in partial axial cross-section.

This eye model is shown schematically in FIG. 4 which shows the cornea 12, the iris 13 and the retina 15.

FIG. 4 includes a schematic representation of the crystalline lens 25.

There follows by way of example a list of the dimensional characteristics of this eye model, as specified in the above referenced article:

radius R4 of the front surface of the cornea 12: 7.72 mm with K=−0.26, radius R5 of the rear surface of the cornea 12: 6.5 mm, thickness E2 of the cornea 12: 0.55 mm, distance D1 from the rear surface of the cornea 12 to the front surface of the crystalline lens 25: 3.05 mm, radius R6 of the front surface of the crystalline lens 25: 10.2 mm with K=−3.1316, radius R7 of the rear surface of the crystalline lens 25: −6 mm with K=−1, thickness E3 of the crystalline lens 25: 4 mm, distance D2 from the rear surface of the crystalline lens 25 to the retina 15: 16.341 mm, radius R8 of the retina 15: −12 mm, refractive index N2 of the cornea 12: 1.367, refractive index N3 of the humor between the cornea 12 and the crystalline lens 25: 1.337, refractive index N4 of the crystalline lens 25: 1.42,
refractive index M5 of the humor between the crystalline lens 25 and the retina 15: 1.336.

Figure 5:
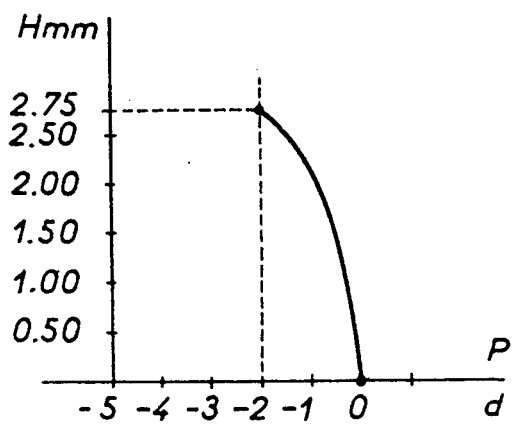
FIG. 5 is a diagram relating to the object proximity curve of the eye model, in isolation.

In FIG. 5 the object proximity P of this model I in diopters d is plotted on the horizontal axis and the distance H from the axis in millimeters is plotted on the vertical axis.

In the absence of any longitudinal spherical aberration a light ray F parallel to the axis A and at a distance H from the axis A intercepts the axis A at the retina 15.

In practice, and as schematically represented in FIG. 4, there is some longitudinal spherical aberration dx' in the corresponding image space.

The object proximity P used in these calculations is defined by the equation:

$$P = \frac{N' \, dx'}{f^2}$$

in which N' is the refractive index of the image medium and f' is the focal length of the eye model.

In practise, N'=1.336.

For convenience it will be assumed that the focal length f' is constant, the effects of variations in it being negligible in practice.

This focal length f' is between 18 and 25 mm, for example.

In this preferred embodiment an arbitrary value of 21.5 mm has been chosen.

On the basis of the foregoing, a ray tracing program can be used to establish point by point the curve representing the object proximity P.

The same process is applied for the optical system comprising, as shown for a particular eye in FIG. 1, the optical component in question and a given eye model such as that shown in FIG. 4 from which the crystalline lens has been eliminated when, as in this instance, the optical component concerned is an intra-ocular implant 10.

In accordance with the invention, however, and as shown in the diagram in FIG. 6 for the intra-ocular implant 10 shown in FIGS. 1 through 3, the numerical parameters R1, K, A2, A3, A4 and A5 are then chosen so that, for this optical system, they yield a representative curve for the object proximity P as defined above which:

for high values of the distance from the axis comprises a substantially straight first section with a slope less than or equal to zero and entirely located between a vertical line passing through a defined reference origin and an oblique line passing through points with coordinates (−1, 1.5) and (−1.5, 2.75) relative to the reference origin;

for low values of the distance from the axis comprises a second section intersecting the diopter axis vertically between points with horizontal coordinates (−2.5) and (−4) relative to the reference origin, and for intermediate values of the distance from the axis comprises a median section merging monotonically and continuously with the first and second sections.

To facilitate the understanding of the invention the sectors within which the sections $T_I$ and $T_{II}$ of the object proximity curve P must lie have been shaded in FIGS. 6 through 18.

The section $T_I$ corresponds to far vision and the section $T_{II}$ to near vision.

In practice, depending on the axial depth of the eye 11 to be treated and/or the radius of curvature of its cornea, far vision is adjusted as necessary by translating the object proximity curve P along the diopters axis, in other words by appropriately adding diopters relative to the selected reference origin 0.

All that is needed to achieve this is to adjust appropriately the radius of one of the spherical surfaces in question.

This surface may be the spherical rear surface 18.

However, it may equally well be the surface with radius R1 of the base sphere of the aspherical surface 22 of the front surface 17.

In the embodiment shown in FIG. 6 the parameters R1, K, A2, A3, A4 and A5 defining this aspherical surface 22 are in practise chosen in such a way that for far vision (section $T_I$) the longitudinal spherical aberration due to the optical system consisting of the optical component and the eye model employed, minus the crystalline lens because the optical component is an intra-ocular implant 10, is substantially the same as that of the eye model alone, complete with its crystalline lens.

In other words the section $T_I$ of the resulting object proximity curve P has a shape substantially analogous to that of the corresponding part of the object proximity curve P of the eye model used.

Be this as it may, the object proximity curve P of the optical system consisting of this eye model and the optical component in accordance with the invention having been determined in this way, an automatic optimizing program may be used to determine the values of the numerical parameters to be used, in particular an optimization program using the damped least squares method. This technique is well known to those skilled in this art.

Instead of being biconvex, the intra-ocular implant 10 in accordance with the invention may be convex-plane, its rear surface 18 having a sufficiently large radius $R_2$ for it to be regarded as a plane.

It may equally well be plane-convex, the radius $R_1$ of the base sphere of the aspherical central part 22 of its front surface 17 being then relatively large.

What is more, instead of being implanted in the anterior chamber 16 of the eye 11 to be treated, the intra-ocular implant 10 in accordance with the invention may equally well be implanted in its posterior chamber.

Furthermore, in a second embodiment of the invention the numerical parameters to be determined may be so chosen that for far vision the longitudinal spherical aberration due to the optical system consisting of the optical component and the eye model used, minus its crystalline lens when, as here, the optical component concerned is an intra-ocular implant 10, is corrected overall.

The section $T_I$ of the corresponding object proximity curve P is then substantially vertical.

Finally, instead of being an intra-ocular implant the optical component in accordance with the invention may equally well be a contact lens.

In this case the crystalline lens of the eye model used is, of course, retained.

Tables T1 and T2 set out with references to FIGS. 6 through 18 the numerical parameters of various optical components in accordance with the invention, showing their nature and where they are implanted, the abbreviation "AC" signifying "anterior chamber" and the abbreviation "PC" signifying "posterior chamber".

Of course, the present invention is not limited to these examples.

TABLE T1

| | Implantation | R1 | K | A2 × $10^{-2}$ | A3 × $10^{-3}$ | A4 × $10^{-4}$ | A5 × $10^{-5}$ | Figure |
|---|---|---|---|---|---|---|---|---|
| Example 1 Biconvex implant | AC | 13.450 | −132.085 | −0.1734521 | 0.6588392 | −0.7577453 | 0.3000454 | 6 |
| Example 2 Convex-plane implant | AC | 6.095 | −14.103 | −0.0003297 | 0.830998 | −1.141028 | 0.5263252 | 7 |
| Example 3 Plane-convex implant | AC | 40.000 | −3002.10 | −0.4500209 | 0.8996099 | −0.9091179 | 0.3379623 | 8 |
| Example 4 Biconvex implant | PC | 12.056 | −140.977 | −0.1222130 | 0.5850626 | −0.6676928 | 0.2301316 | 9 |
| Example 5 Convex-plane implant | PC | 5.526 | −14.4675 | 0.0812567 | 0.933811 | −1.468438 | 0.7497366 | 10 |
| Example 6 Plane-convex implant | PC | 30.000 | −1498.67 | −0.5268837 | 1.219160 | −1.408936 | 0.6006825 | 11 |
| Example 7 Biconvex implant | AC | 13.418 | −145.681 | −0.1241714 | 0.5080515 | −0.6844913 | 0.3231505 | 12 |
| Example 8 Convex-plane implant | AC | 6.106 | −12.8283 | −0.0133428 | 0.7439685 | −1.067136 | 0.5192035 | 13 |
| Example 9 Plane-convex implant | AC | 40.000 | −3921.44 | −0.3759112 | 0.5819191 | −0.5171569 | 0.1652432 | 14 |
| Example 10 Biconvex implant | PC | 12.149 | −132.152 | −0.1261559 | 0.5283329 | −0.7105776 | 0.3258733 | 15 |
| Example 11 Convex-plane implant | PC | 5.548 | −12.5946 | 0.0382755 | 0.8435873 | −1.344659 | 0.7089764 | 16 |
| Example 12 Plane-convex implant | PC | 40.000 | −3722.72 | −0.5627028 | 1.135583 | −1.357986 | 0.6273719 | 17 |
| Example 13 Contact lens | | 7.24 | −6.90497 | 0.0355294 | 0.2450409 | −0.2881221 | 0.1164780 | 18 |

TABLE T2

| | Implantation | R2 | N1 | E1 | R3 | X3 | Y3 | Figure |
|---|---|---|---|---|---|---|---|---|
| Example 1 Binconvex implant | AC | −14 | 1.4920 | 0.78 | 32.7362 | 32.7130 | −0.8122 | 6 |
| Example 2 Convex-plane implant | AC | 40 | 1.4920 | 0.79 | 7.4785 | 7.4844 | −0.0287 | 7 |
| Example 3 Plane-convex implant | AC | −8.047 | 1.4920 | 0.78 | −20.4506 | −20.4528 | 1.4649 | 8 |
| Example 4 Biconvex implant | PC | −12.5 | 1.4920 | 0.78 | 45.3353 | 45.2308 | −2.3653 | 9 |
| Example 5 Convex-plane implant | PC | 40 | 1.4920 | 0.80 | 6.7762 | 6.7850 | −0.0131 | 10 |
| Example 6 Plane-convex implant | PC | −7.555 | 1.4920 | 0.78 | −17.0687 | −17.0671 | 1.6757 | 11 |
| Example 7 Biconvex implant | AC | −14 | 1.4920 | 0.77 | 75.7360 | 75.6005 | −3.9158 | 12 |
| Example 8 Convex-plane implant | AC | 40 | 1.4920 | 0.77 | 8.5249 | 8.5068 | −0.2525 | 13 |
| Example 9 Plane-convex implant | AC | −8.028 | 1.4920 | 0.76 | −15.2978 | −15.3005 | 1.4775 | 14 |
| Example 10 Biconvex implant | PC | −12.5 | 1.4920 | 0.77 | 124.6802 | 124.3391 | −8.5209 | 15 |
| Example 11 Convex-plane implant | PC | 40 | 1.4920 | 0.78 | 7.6571 | 7.6465 | −0.1999 | 16 |
| Example 12 Plane-convex implant | PC | −7.095 | 1.4920 | 0.77 | −11.3372 | −11.3455 | 1.4363 | 17 |
| Example 13 Contact lens | | 7.7200 | 1.377 | 0.22 | | | | 18 |

There is claimed:

1. Sight-correcting optical component having front and rear surfaces at least one of which has a central part in the form of an aspherical surface of revolution with a meridian section satisfying the equation $$X = \frac{1}{R}\left[\frac{Y^2}{1 + \sqrt{1 - (1 + K) Y^2/R^2}}\right] + A2\, Y^4 + A3\, Y^6 + A4\, Y^8 + A5\, Y^{10}$$

in which R1, K, A2, A3, A4 and A5 are numerical parameters chosen so that for the optical system comprising said optical component and a specified eye model, minus the crystalline lens if said optical component is an intra-ocular implant, they yield for an object proximity P defined by the equation $$P = N' \cdot \frac{dx'}{f'^2}$$

in which N' is the refractive index of the image medium, dx' is the longitudinal spherical aberration in the image space and f' is the focal length of said eye model, a representative curve which:

for high values of the distance from the axis comprises a substantially straight first section with a slope less than or equal to zero and entirely located between a vertical line passing through a defined reference origin and an oblique line passing through points with coordinates (−1, 1.5) and (−1.5, 2.75) relative to said reference origin;

for low values of the distance from the axis comprises a second section intersecting the diopter axis vertically between points with horizontal coordinates (−2.5) and (−4) relative to said reference origin, and for intermediate values of the distance from the axis comprising a median section merging monotonically and continuously with said first and second sections.

2. Optical component according to claim 1 wherein said numerical parameters are chosen so that for far vision the longitudinal spherical aberration due to the optical system comprising the optical component and the eye model used, minus the crystalline lens where appropriate, is substantially the same as that for the eye model alone, complete with its crystalline lens 3. Optical component according to claim 1 wherein said numerical parameters are chosen so that for far vision the longitudinal spherical aberration due to the optical system comprising the optical component and said eye model, minus the crystalline lens where appropriate, is substantially corrected.

4. Optical component according to claim 1 wherein said eye model is an accommodation-dependent model for reproducing an increment of refractive power of an eye during accommodation.

5. Optical component according to claim 1 wherein the peripheral part of the surface having an aspherical surface in its center comprises a toroidal surface whose radius of curvature is equal to that of said aspherical surface where it merges there with.

6. Optical component according to claim 1 wherein said aspherical surface is delimited by a circumference having a radius less than or equal to 2.35 mm.

7. Optical component according to claim 1 wherein the refractive index of the image medium is 1.336.

8. Optical component according to claim 1 wherein the focal length of said eye model is constant.

9. Optical component according to claim 8 wherein said focal length is between 18 and 25 mm.

10. Optical component according to claim 9 wherein said focal length is 21.5 mm.

11. Optical component according to claim 1 in the form of an intra-ocular implant.

12. Optical component according to claim 1 in the form of a contact lens.

* * * * *